United States Patent [19]

Freitag et al.

[11] 4,307,039

[45] Dec. 22, 1981

[54] PROCESS FOR THE PREPARATION OF AROMATIC DICARBOXYLIC ACID DICHLORIDES

[75] Inventors: Dieter Freitag, Krefeld, Fed. Rep. of Germany; Manfred Schmidt, New Martinsville, W. Va.

[73] Assignee: Bayer Aktiengesellschaft, Fed. Rep. of Germany

[21] Appl. No.: 164,287

[22] Filed: Jun. 30, 1980

[30] Foreign Application Priority Data

Jul. 3, 1979 [DE] Fed. Rep. of Germany ....... 2926779

[51] Int. Cl.³ .............................................. C07C 51/60
[52] U.S. Cl. ................................................. 260/544 K
[58] Field of Search .................................... 260/544 K

[56] References Cited

U.S. PATENT DOCUMENTS 3,544,626 12/1970 Carr et al. ...................... 260/544 K Primary Examiner—Natalie Trousof
Assistant Examiner—L. Hendriksen
Attorney, Agent, or Firm—Connolly and Hutz

[57] ABSTRACT

A single-stage process for the preparation of high purity aromatic dicarboxylic acid dichlorides by reacting an aromatic dicarboxylic acid or an aromatic dicarboxylic acid mixture with phosgene in the presence of betaines as catalysts and optionally in a solvent or diluent, and the application of the aromatic dicarboxylic acid dichlorides for making polycondensates.

2 Claims, No Drawings

PROCESS FOR THE PREPARATION OF AROMATIC DICARBOXYLIC ACID DICHLORIDES

This invention relates to a single-stage process for the preparation of high purity aromatic dicarboxylic acid dichlorides capable of polycondensation.

The preparation of aliphatic and aromatic acid chlorides by reacting a carboxylic acid with phosgene is described in U.S. Pat. Nos. 3,184,506; 3,544,626; 3,544,627 and 3,547,960 and in German Offenlegungsschrift Nos. 2,400,007 and 2,321,122. In these processes, dark-coloured carboxylic acid chlorides having a purity of from 96 to 99% are obtained as reaction products. Aromatic dicarboxylic acid dichlorides having this low degree of purity cannot be directly used in the two-phase interfacial polycondensation process for the preparation of high molecular weight polycondensates, such as aromatic polyamides or aromatic polyesters. The content of unreacted or only semi-reacted dicarboxylic acids thereof interferes with the polycondensation reaction, causes undesirable chain-termination and results in polymers containing terminal carboxyl groups. The thus-obtained aromatic dicarboxylic acid dichlorides are dark-coloured as a result of the presence of impurities and contain troublesome carbamic acid chlorides formed by reaction with the catalysts (cf. Chem. Ref. 1973, Vol. 73, No. 1, page 77 or Angewandte Chemie (1974), Vol. 1962, No. 21, page 864).

In order to obtain colourless dicarboxylic acid dichlorides, the crude products have to be purified by recrystallisation or distillation. This involves additional outlay and reduces the yield. In the case of aromatic dicarboxylic acid dichlorides, there is a danger of spontaneous decomposition.

The present invention relates to a single-stage process for the preparation of pure aromatic dicarboxylic acid dichlorides by reacting an aromatic dicarboxylic acid with phosgene in the presence of a catalyst and optionally in a solvent and/or diluent, wherein betaines are used as catalysts. The thus-obtained aromatic dicarboxylic acid dichlorides are substantially colourless and, apart from the catalysts used, contain 0.1% of impurities or less, so that they may be used without further purification in the preparation of colourless, high molecular weight polycondensates.

The betaines used as catalysts in the process according to the present invention do not adversely affect the preparation of aromatic polyesters, for example, on the one hand, because, as phase transfer catalysts, they accelerate the reaction of the aromatic dicarboxylic acid dichlorides with bisphenols by the two-phase interfacial polycondensates process and, on the other hand, because they are soluble in alkaline, aqueous medium, so that they can readily be separated from the organic solution of the polycondensate by the washing operations of the process.

Suitable catalysts according to the present invention are betaines having one of the following structures (I), (II) or (III):

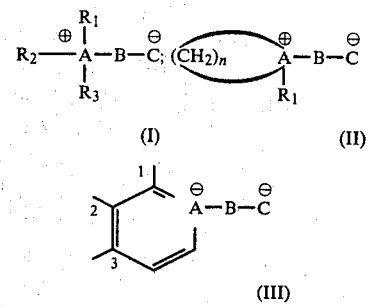

wherein
A represents N or P;
C represents $-SO_3{}^\ominus$ or $-COO^\ominus$;
B represents a $C_1$ or $C_2$ alkylene radical, a $C_6$–$C_{16}$ cycloalkylene, aryl or alkyl aryl radical;
$R_1$, $R_2$ and $R_3$, which may be the same or different, may represent a $C_1$–$C_{12}$ alkyl radical, a $C_6$–$C_{15}$ aryl or alkyl aryl or aralkyl radical;
n in structure (II) represents 4 or 5, and the aromatic ring containing the heteroatom A in structure (III) may optionally be substituted by from 1 to 4 $C_1$–$C_4$ alkyl radicals or by from 1 to 4 halogen atoms, such as F, Cl, or Br, or may be fused with another aromatic ring in the 1-2 position or in the 2-3 position.

The following individual compounds, for example, are suitable:

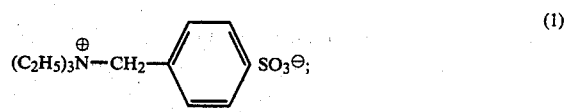

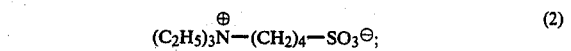

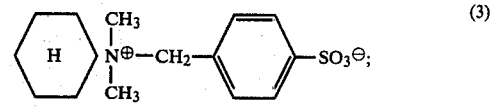

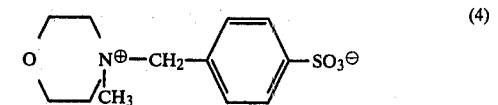

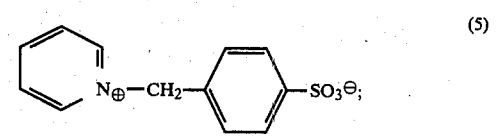

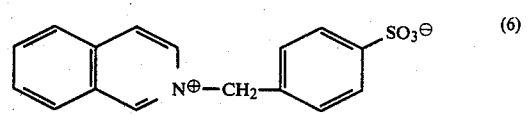

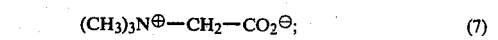

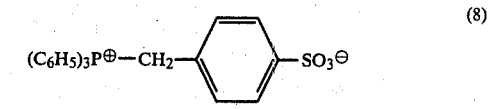

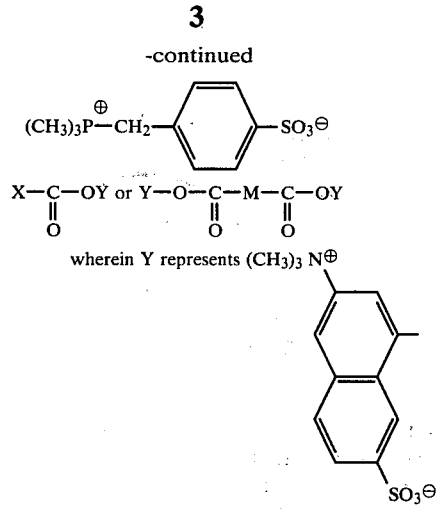

wherein Y represents $(CH_3)_3 N^{\oplus}$

X represents $C_1$–$C_{10}$ alkyl or $C_6$–$C_{10}$ aryl;
M represents a single bond, a $C_2$–$C_8$ alkylene radical or a $C_6$–$C_{10}$ arylene radical.

(1) p-(triethyl ammonium-methyl)-benzene-sulphobetaine,
(2) triethyl-butyl ammonium-4-sulphobetaine,
(4) p-(dimethyl-morpholino)-benzene-sulphobetaine,
(5) p-(pyridinium-methyl)-benzene-sulphobetaine,
(6) p-(isoquinolinium-methyl)-benzene-sulphobetaine,
(7) trimethyl glycine="betaine",
(8) p-(triphenyl phosphonium-methyl)-benzene-sulphobetaine,
(9) p-(tetramethyl phosphonium)-benzene-sulphobetaine.

The following individual compounds are particularly suitable:

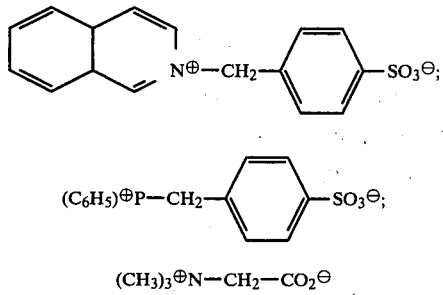

$(CH_3)_3{}^{\oplus}N-CH_2-CO_2{}^{\ominus}$ (7)

According to the present invention, the betaines are used in quantities of from 0.1 to 3%, by weight, preferably from 0.2 to 1.5%, by weight, based on the aromatic dicarboxylic acids used.

Aromatic dicarboxylic acids correspond to the following general formulae:

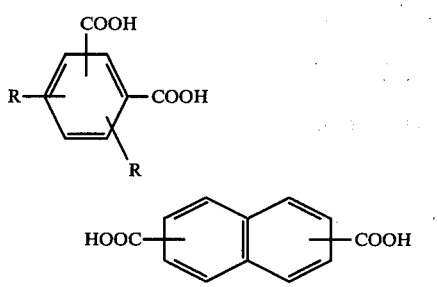

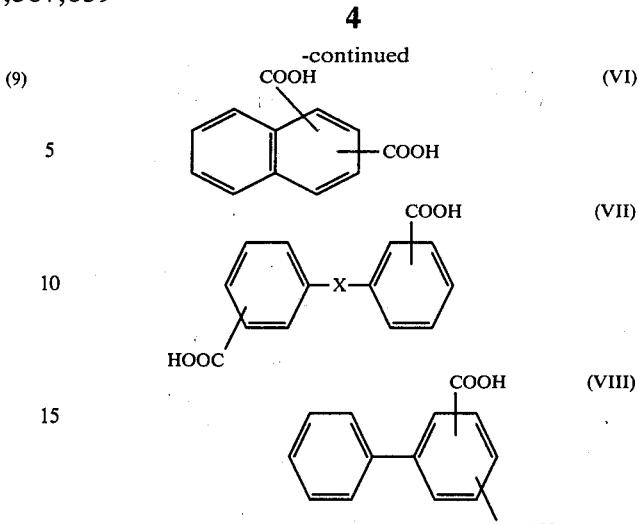

wherein
R represents H, $C_1$–$C_4$ alkyl or halogen (preferably chlorine or bromine); and
X represents a single bond, —O—, —S—,

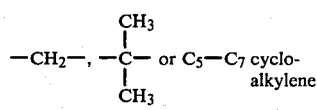

Mixtures can also be used.

Examples of aromatic dicarboxylic acids are phthalic acid, isophthalic acid, terephthalic acid, mixtures of isophthalic and terephthalic acids, diphenic acid and 1,4-naphthalene dicarboxylic acid.

The solvents or diluents used are preferably the aromatic dicarboxylic acid dichlorides or (in the case of mixtures) dichlorides formed during the reaction. Inert diluents, such as aliphatic or aromatic hydrocarbons, halogen-substituted aromatic hydrocarbons, halogen-substituted aliphatic hydrocarbons or saturated aliphatic ethers, can also be used. The reaction temperature is generally from 70° to 180° C., preferably from 100° to 160° C.

The molar ratio of aromatic dicarboxylic acid to phosgene is preferably from 1:2 to 1:2.5, i.e. a small excess of phosgene is advisable in order to replace the losses arising during the removal of $CO_2$- and HCl-gas from the reaction mixture during phosgenation.

The process according to the present invention can be carried out either continuously or in batches. In one continuous embodiment, a solution of aromatic dicarboxylic acid, dicarboxylic acid dichloride and catalyst is passed downwards through a reaction tube in countercurrent to ascending phosgene gas and aromatic dicarboxylic acid dichloride and catalyst are removed at the foot of the reaction tube.

In one batch-type embodiment of the process, aromatic dicarboxylic acid, aromatic dicarboxylic acid dichloride and catalyst are initially introduced under normal pressure. They are then heated with stirring to from 70° to 160° C., as a result of which the aromatic dicarboxylic acid is completely or partly dissolved. From 2 to 2.5 moles of gaseous phosgene per mole of aromatic dicarboxylic acid are then introduced at that temperature. After the removal of excess phosgene, HCl- and $CO_2$-gas by the brief application of vacuum, a residue is obtained of which ≧99.9% consists of aromatic dicarboxylic acid dichloride in addition to the quantity of betaine catalyst used and which can be reacted without further purification to form high molecular weight colourless polycondensates.

EXAMPLE 1

203 g (1 mole) of isophthalic acid dichloride, 166 g of isophthalic acid (1 mole) and 0.8 g of

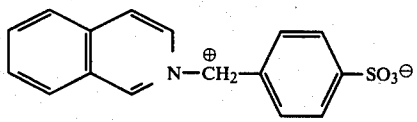

are heated to 148° C. in a spherical flask equipped with a thermometer, stirrer and intensive cooler maintained at −20° C. by cooling brine. Phosgene is then introduced with stirring and refluxing at from 148° to 157° C. until the temperature prevailing in the reaction mixture falls to 146° C.

After cooling to 120° C., a water jet vacuum is applied to remove excess phosgene and HCl- and $CO_2$-gas dissolved in the reaction mixture.

Yield: 406.5 g of a colourless residue of 0.8 g of the betaine catalyst used and 405.7 g of a 100% isophthalic acid dichloride (as determined by titrimetry).

EXAMPLE 2

101.5 g (0.5 mole) of isophthalic acid dichloride, 101.5 g (0.5 mole) of terephthalic acid dichloride, 83 g (0.5 mole) of isophthalic acid, 83 g (0.5 mole) of terephthalic acid and 0.8 g of

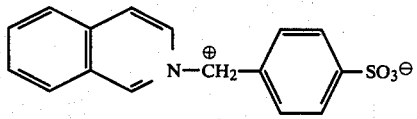

are reacted with phosgene in the same way as in Example 1.

Yield: 406.8 g of a colourless residue of which 0.8 g consists of the betaine catalyst used and 406 g of a mixture of 100% isophthalic and terephthalic acid dichloride (as determined by titrimetry).

EXAMPLE 3

101.5 g (0.5 mole) of isophthalic acid dichloride, 101.5 g (0.5 mole) of terephthalic acid dichloride, 83 g (0.5 mole) of isophthalic acid, 83 g (0.5 mole) of terephthalic acid and 0.8 g of

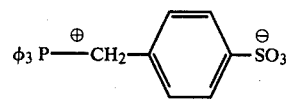

are reacted with phosgene in the same way as in Example 1.

Yield: 406 g of 99.9% isophthalic and terephthalic acid dichloride and 0.8 g of the betaine catalyst used.

EXAMPLE 4

101.5 g (0.5 mole) of isophthalic acid dichloride, 101.5 g (0.5 mole) of terephthalic acid dichloride, 83 g (0.5 mole) of isophthalic acid, 83 g (0.5 mole) of terephthalic acid and 0.3 g of $(CH_3)_3N^{\oplus}—CH_2—CO_2^{\ominus}$ are reacted with phosgene in the same way as in Example 1.

Yield: 406 g of a substantially colourless residue of 0.3 g of catalyst and 405.7 g of a mixture of 100% isophthalic and terephthalic acid dichloride (as determined by titrimetry).

We claim:

1. A process for preparing aromatic dicarboxylic acid dichloride which comprises reacting an aromatic dicarboxylic acid with phosgene in the presence of a catalytic amount of a catalyst selected from the group consisting of

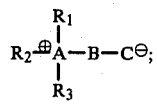

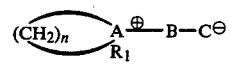

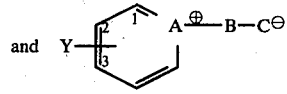

wherein A is N or P; C is —SO$_3^{\ominus}$ or —COO$^{\oplus}$; B is methylene or ethylene, $C_6$-$C_{16}$ cycloalkylene, $C_6$-$C_{16}$ arylene or $C_6$-$C_{16}$ alkarylene; $R_1$ and $R_2$ and $R_3$ are each $C_1$-$C_{12}$ alkyl, $C_6$-$C_{15}$ aryl, $C_6$-$C_{15}$ alkaryl or $C_6$-$C_{15}$ aralkyl; n is 4 or 5 and Y is hydrogen, 1 to 4 $C_1$-$C_4$ alkyl, 1 to 4 halogen, an aromatic ring fused in the 1,2 position or an aromatic ring fused in the 2,3 position.

2. A process of claim 1 wherein said reaction is carried out in the presence of an inert or diluent.

* * * * *